United States Patent
DeVries

[19]

[11] Patent Number: 6,042,576
[45] Date of Patent: Mar. 28, 2000

[54] TWO-STAGE ANGLED VENOUS CANNULA

[75] Inventor: James H. DeVries, Grand Rapids, Mich.

[73] Assignee: Medtronic, Inc., Minneapolis, Minn.

[21] Appl. No.: 08/965,991

[22] Filed: Nov. 7, 1997

Related U.S. Application Data

[63] Continuation of application No. 08/635,832, Apr. 22, 1996, abandoned.

[51] Int. Cl.[7] .................................................. A61M 25/00
[52] U.S. Cl. ........................... 604/523; 604/264; 604/532
[58] Field of Search ................................... 604/523, 525, 604/530, 532, 264, 35, 500, 503

[56] References Cited

U.S. PATENT DOCUMENTS

| | | | |
|---|---|---|---|
| 4,129,129 | 12/1978 | Amrine | 128/214 R |
| 4,248,224 | 2/1981 | Jones | 128/214 R |
| 4,309,994 | 1/1982 | Grunwald | 128/214 R |
| 4,639,252 | 1/1987 | Kelly et al. | 604/282 |
| 4,755,176 | 7/1988 | Patel | 604/280 |
| 4,801,297 | 1/1989 | Mueller | 604/280 |
| 4,804,359 | 2/1989 | Grunwald et al. | 604/4 |
| 5,188,619 | 2/1993 | Myers | 604/280 |
| 5,395,353 | 3/1995 | Scibner | 604/264 |
| 5,425,724 | 6/1995 | Akins | 604/284 |

OTHER PUBLICATIONS

Proceedings of the Society for Experimental Biology and Medicine vol. 75 (Oct.–Dec., 1950 (inclusive).

*Primary Examiner*—John D. Yasko
*Attorney, Agent, or Firm*—Harold R. Patton; Michael J. Jaro

[57] ABSTRACT

A two-staged venous cannula is disclosed having an angled bend near the distal end. In a preferred embodiment, the angle is a right angle. The angle bend allows the cannulation to take place near the junction of the inferior vena cava and the right atrium instead of higher in the right atrium. The cannula has a drainage hole at the apex of the angled bend to act as a blood collection port and a drainage hole at the distal end of the cannula to drain the inferior vena cava. The two-stage venous cannula is made of a rigid material at its distal end so that the distal end of the cannula may be easily inserted into the patient's heart through the right atrium. The disclosed cannula keeps the cannula away from the aorta, allows the cannula to exit the superior vena cava at an angle more perpendicular to the axis of the superior vena cave and allows the cannula to be used in minimally invasive surgical procedures where size and access restrictions often make it difficult to place and maintain such devices.

3 Claims, 5 Drawing Sheets

TWO-STAGE ANGLED VENOUS CANNULA

This application is a continuation, of application Ser. No. 08/653,832 filed Apr. 22, 1996, now abandoned.

BACKGROUND OF THE INVENTION

1. Field of the Invention

This invention relates to an invention for draining blood from the right atrium of a heart and more specifically relates to a relatively rigid two stage venous cannula with an angled bend and a drainage hole located at the apex of the bend.

2. Description of Related Art

During cardiac surgery, it is often desirable to maintain circulation of blood through a patient's body. This is often done by connecting a patient to an extra-corporeal system that adds oxygen to and removes carbon dioxide from the blood, heats or cools the blood and provides impetus to the blood to cause the blood to circulate through the patient's vascular system.

It is necessary to connect the patient to the extra-corporeal circuit. This is usually done by inserting cannula into the patient's venous system near or in the heart to remove blood from the patient and direct it to the extra-corporeal circuit. After the blood has passed through the extra-corporeal circuit, the blood in infused into the patient's arterial system near the heart.

One way of removing venous blood from a patient is shown in FIG. 1. Two single-stage cannulae 2,4 are used. Both cannulae 2,4 are right-angle cannulae with a distal end 6,8 respectively. Each cannula 2,4 has openings 10,12 at the distal end 6,8, respectively.

Cannula 2 is placed in the patient's superior vena cava 14 through an opening 16 in the superior vena cava 14. The distal end 6 is directed away from the heart 18 so that opening 10 removes blood moving toward the heart 18 through the superior vena cava 14.

In like manner, cannula 4 is placed in the patient's inferior vena cava 20 through an opening 22 in the inferior vena cava 20. The distal end 8 is directed away from the heart 18 so that opening 12 removes blood moving toward the heart 18 through the inferior vena cava 20. Both cannulae 2,4 are joined together at a Y-connector (not shown) to form a single line of blood flow into the extra-corporeal circuit.

A disadvantage of this type of system is that two cannulae 2,4 must be used. In addition, two holes 16,22 must be placed in the patient's vascular system. It is preferable to use only a single cannula and to require only a single hole in the patient's vascular system, especially when the right atrium will not be surgically opened. Therefore, a two-stage cannulation system, such as is shown in FIG. 2, has been developed.

The previously known two-stage cannula 22 has openings 24 at the distal end 26 of the cannula and at least one opening 28 a distance from the distal end 26. In use, an opening 30 is made high in the patient's right atrium 32 and cannula 22 is inserted therethrough. The distal end 26 is advanced until it passes through the right atrium 32 and into the inferior vena cava 20. Opening 28 is located along cannula 22 so that opening 28 is located in the right atrium 32 when opening 24 is in the inferior vena cava 20.

In use, blood entering the right atrium 32 through the superior vena cava 14 is removed through opening 28. Blood flowing in the inferior vena cava 20 is removed through opening 24 before the blood enters the right atrium 32. Any blood entering the right atrium 32 from the inferior vena cava 20 is removed through opening 28. This allows a single two-stage venous cannula 22 to simultaneously drain the right atrium 32 and superior vena cava 14 through opening 28 while the inferior vena cava 20 is drained through opening 24 at the distal end 26 of cannula 22.

The two-stage venous cannula was introduced by Sarns, Inc. of Ann Arbor, Mich. to the cardiac surgery market in the late 1970's as an alternative to bi-caval venous cannulation on procedures for coronary artery by-pass grafts (CABG). U.S. Pat. No. 4,129,129, issued to Bruce A. Amrine on Dec. 12, 1978 and U.S. Pat. No. 4,639,252 issued to Michael N. Kelly, et al. on Jan. 27, 1987 disclose two-stage venous cannulae.

These previously known two-stage cannulae have been made of flexible material so that the cannula may bend as needed to be placed into and remain in the patient's inferior vena cava 20 and right atrium 32. A problem with such a cannula is that because of the flexible nature of the cannula, it is often difficult to insert, advance and position the cannula as desired.

An additional problem with previously known cannulae is that the cannulation site is located in the right atrium. This places the cannula near the aorta. Having the cannula near the aorta is potentially troublesome because the cannula may block visibility and access to areas of surgical interest in the heart.

SUMMARY OF THE INVENTION

A two-staged venous cannula is disclosed having an angled bend near the distal end. In a preferred embodiment, the angle is a right angle. The angle bend allows the cannulation to take place near the junction of the inferior vena cava and the right atrium instead of in the right atrium. The cannula has a drainage hole at the apex of the angled bend to act as a blood collection port and a drainage hole at the distal end of the cannula to drain the inferior vena cava. The two-stage venous cannula is made of a rigid material at its distal end so that the distal end of the cannula may be easily inserted into the patient's heart through the superior vena cava.

The disclosed cannula keeps the cannula away from the aorta. In addition, the angled design of the cannula allows the cannula to exit the right atrium at an angle more perpendicular to the axis of the superior and inferior vena cavae. This produces a more convenient and possibly shorter connection from the cannula to the extra-corporeal circuit.

Further, the angled and rigid distal end design of the cannula allows the cannula to be used in minimally invasive surgical procedures where size and access restrictions often make it difficult to place and maintain such devices.

A key feature of this cannula is the ability of the cannula to be inserted, advanced and positioned in the patient's vascular system.

Another key feature of this cannula is the ability of the cannula to place the cannulation site near the junction of the inferior vena cava and the right atrium instead of in the right atrium.

It is therefore a primary object of the invention to provide a two-stage venous cannula that is easy to insert, advance and position.

It is another primary object of the invention to provide a two-stage venous cannula that places the cannulation site near the junction of the inferior vena cava and the right atrium instead of in the right atrium.

It is another primary object of the invention to provide a two-stage venous cannula that places the cannula away from the aorta.

It is yet another primary object of the invention to provide a two-stage venous cannula that allows the cannula to exit the right atrium at an angle more perpendicular to the axis of the superior and inferior vena cavae.

It is another object of the present invention to provide a venous cannula that requires only a single small incision to place and use the cannula.

These and other objects and advantages of the invention will be clear from the description contained herein and more particularly with reference to the following detailed description of the invention with its accompanying reference to the attached drawings. Throughout the description, like elements, wherever mentioned, are referred to with like reference numbers.

DETAILED DESCRIPTION OF THE INVENTION

Figure 1:
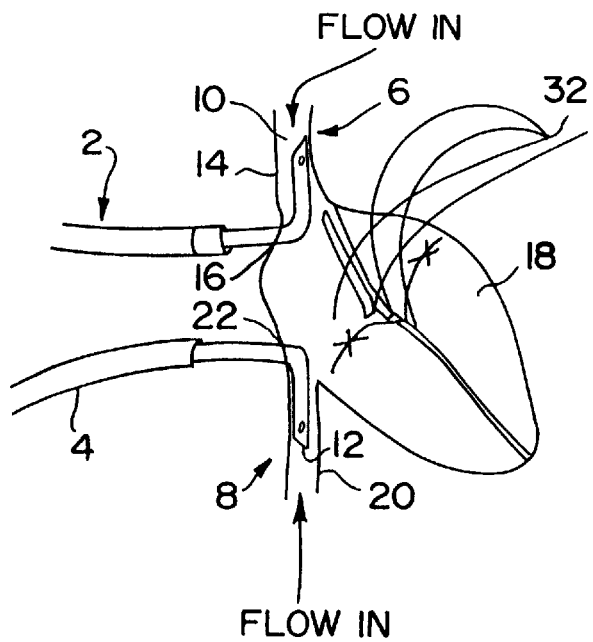
FIG. 1 is a side schematic view of a conventional bi-caval cannulation using two right-angle venous cannulae.
Figure 2:
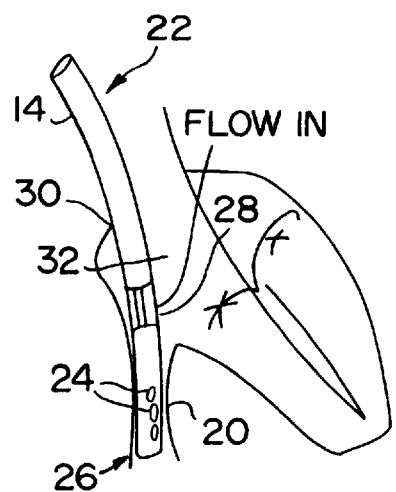
FIG. 2 is a side schematic view of a conventional two-stage cannula in use in a heart.
Figure 3:
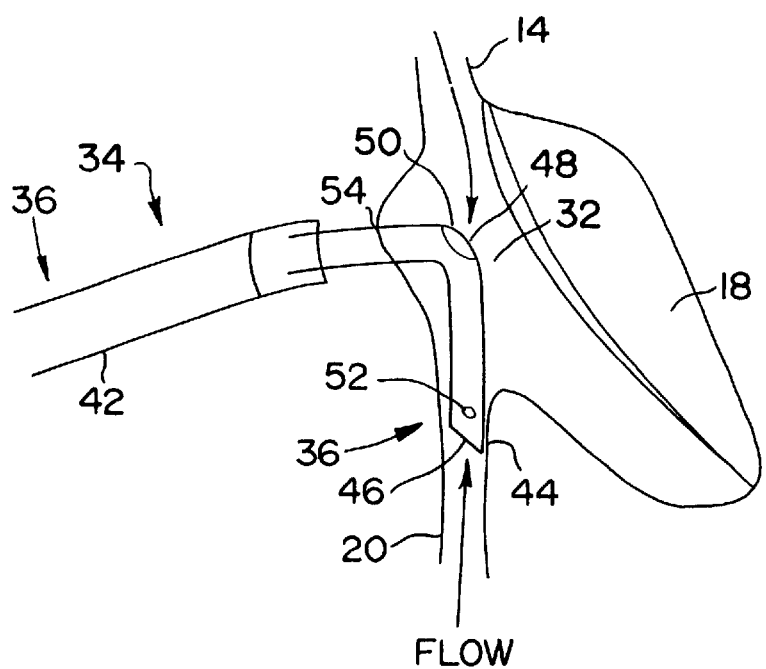
FIG. 3 is a perspective view of the angled two-stage cannula of the present invention with the angle being a right angle.
Figure 4:
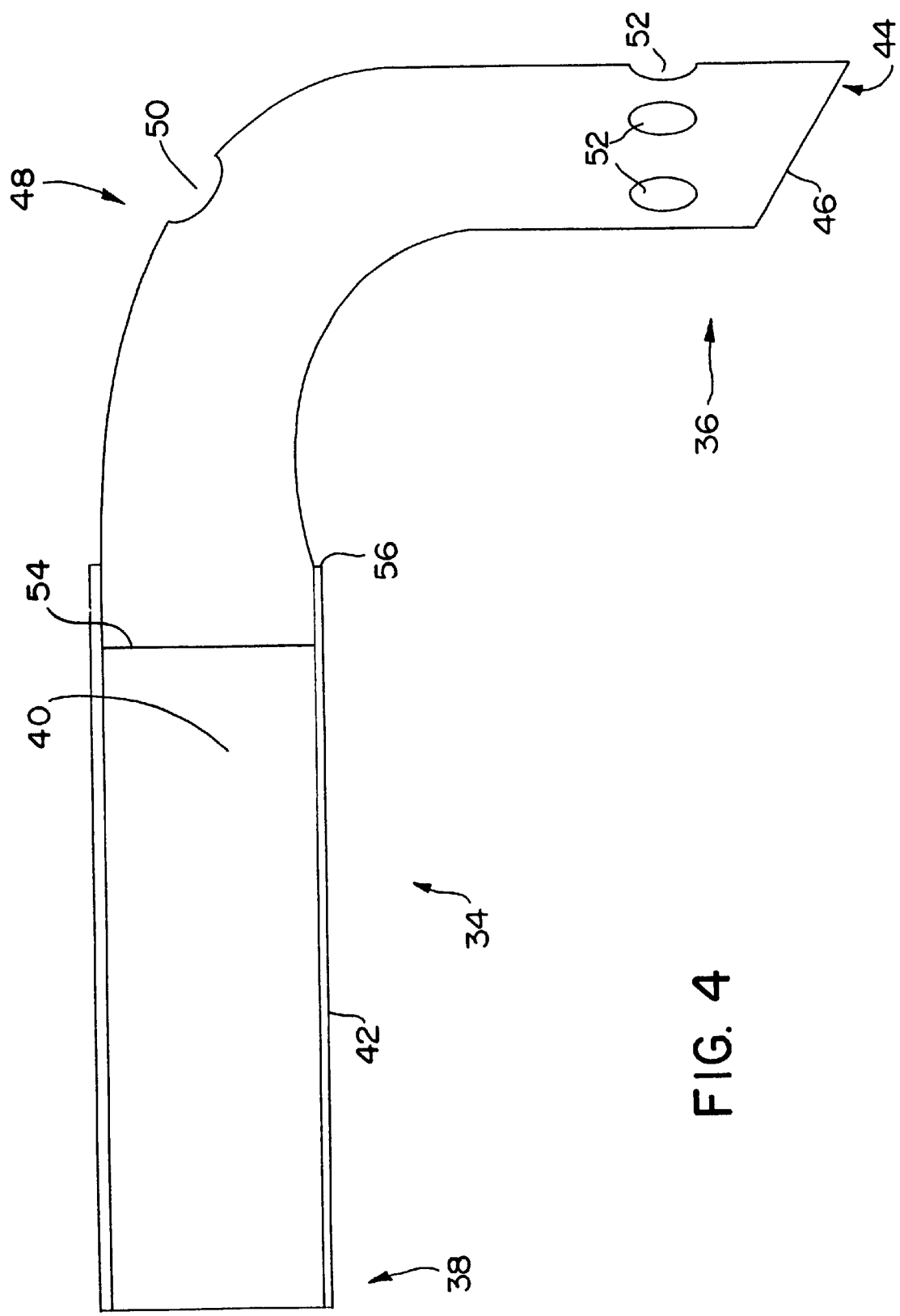
FIG. 4 is a side cross-sectional view of the angled two-stage cannula of FIG. 3.

FIG. 3 shows a perspective view of a two-staged venous cannula according to the present invention, generally labeled 34. Cannula 34 has a distal end 36 and a proximal end 38 and an interior lumen 40 extending from the distal end 36 to the proximal end 38. Cannula 34 is comprised of an elongated tubular body 42 (FIG. 4). Interior lumen 40 is open at the proximal end 36 to allow canula 34 to be connected to an extra-corporeal cardiac bypass system. As will be explained hereafter, in one embodiment, interior lumen 40 is also open at the ultimate distal end 44 to form an opening 46.

Figure 5:
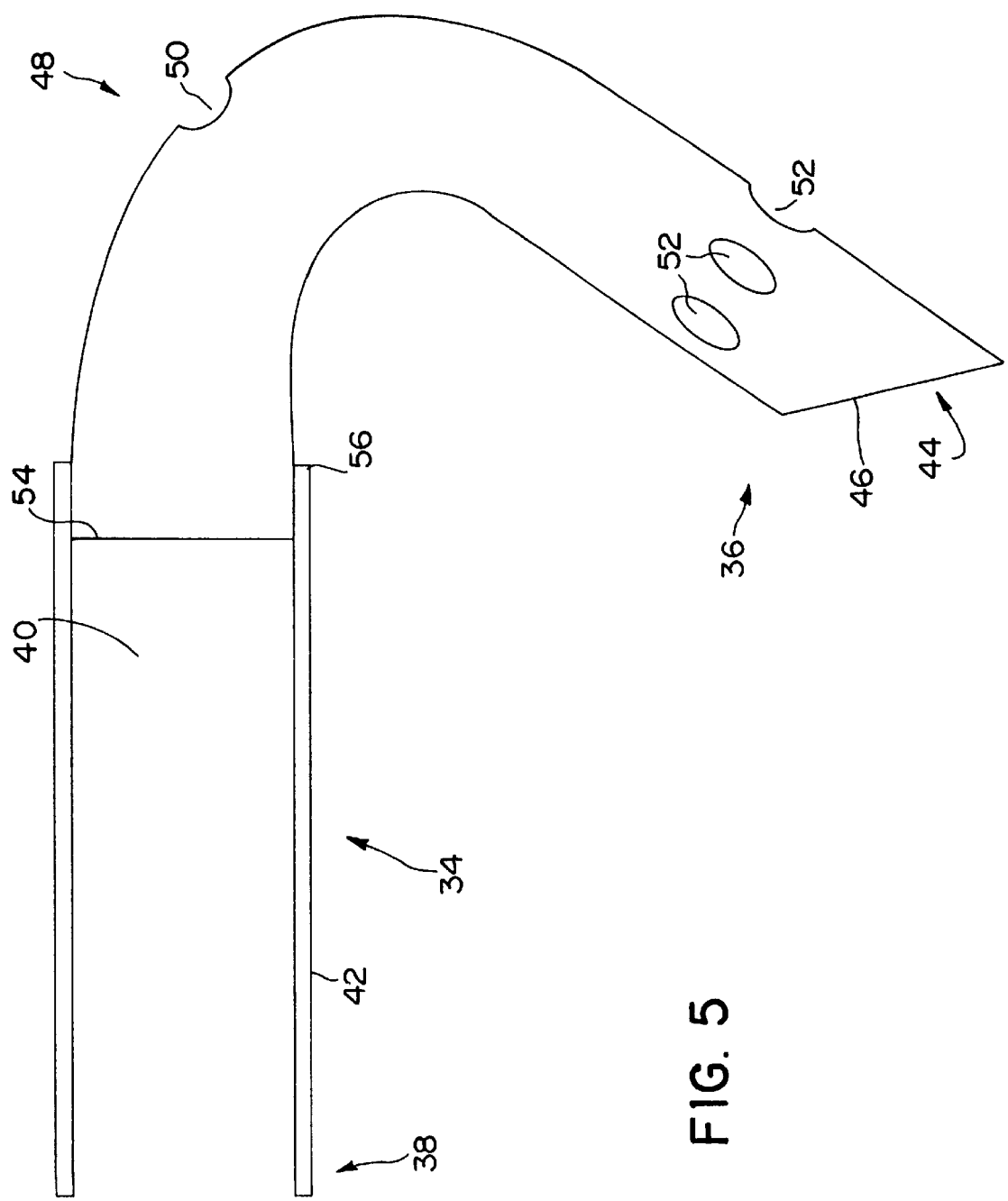
FIG. 5 is a side cross-sectional view of the angled two-stage cannula of the present invention with the angle being an acute angle.
Figure 6:
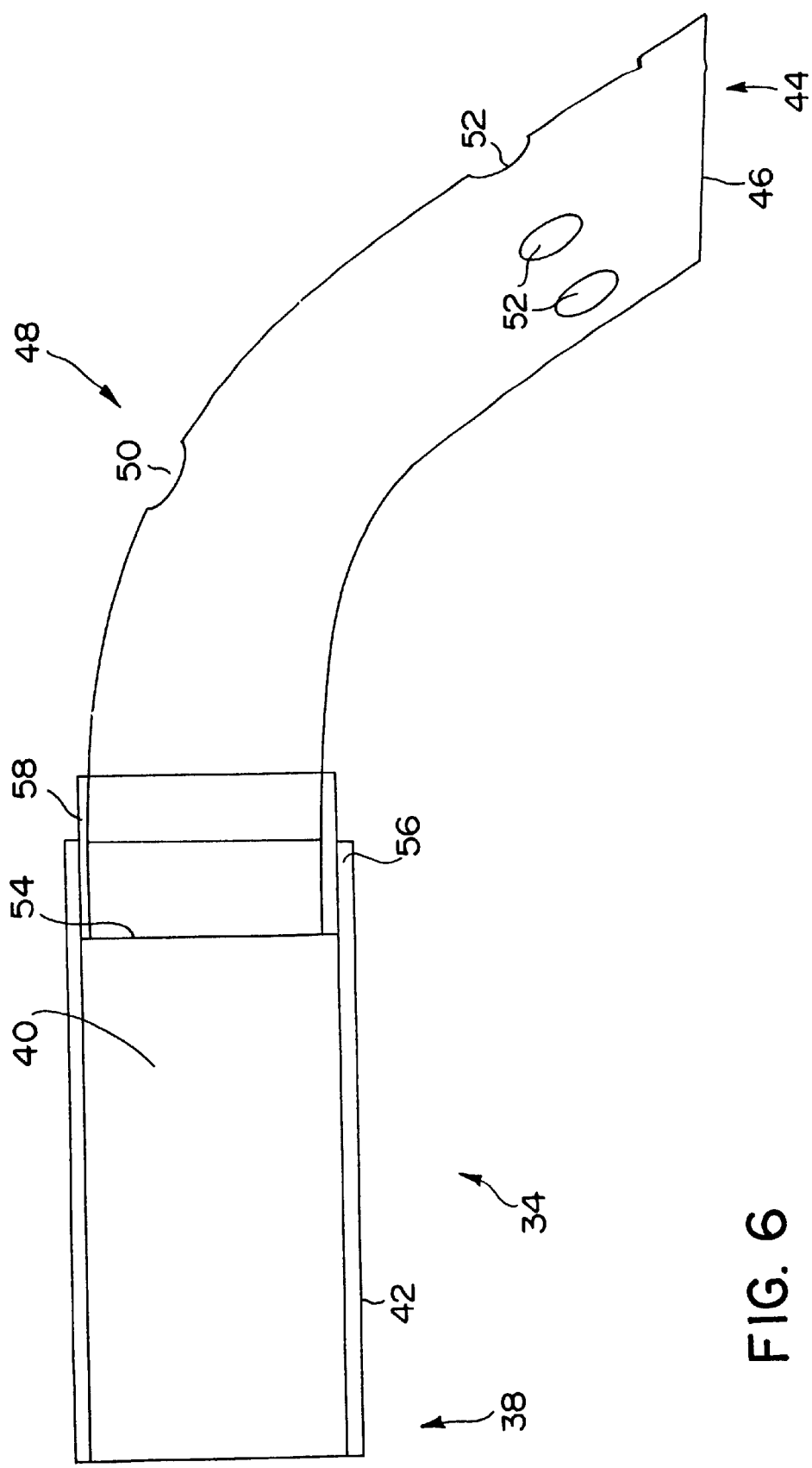
FIG. 6 is a side cross-sectional view of the angled two-stage cannula of the present invention with the angle being an obtuse angle.
Figure 7:
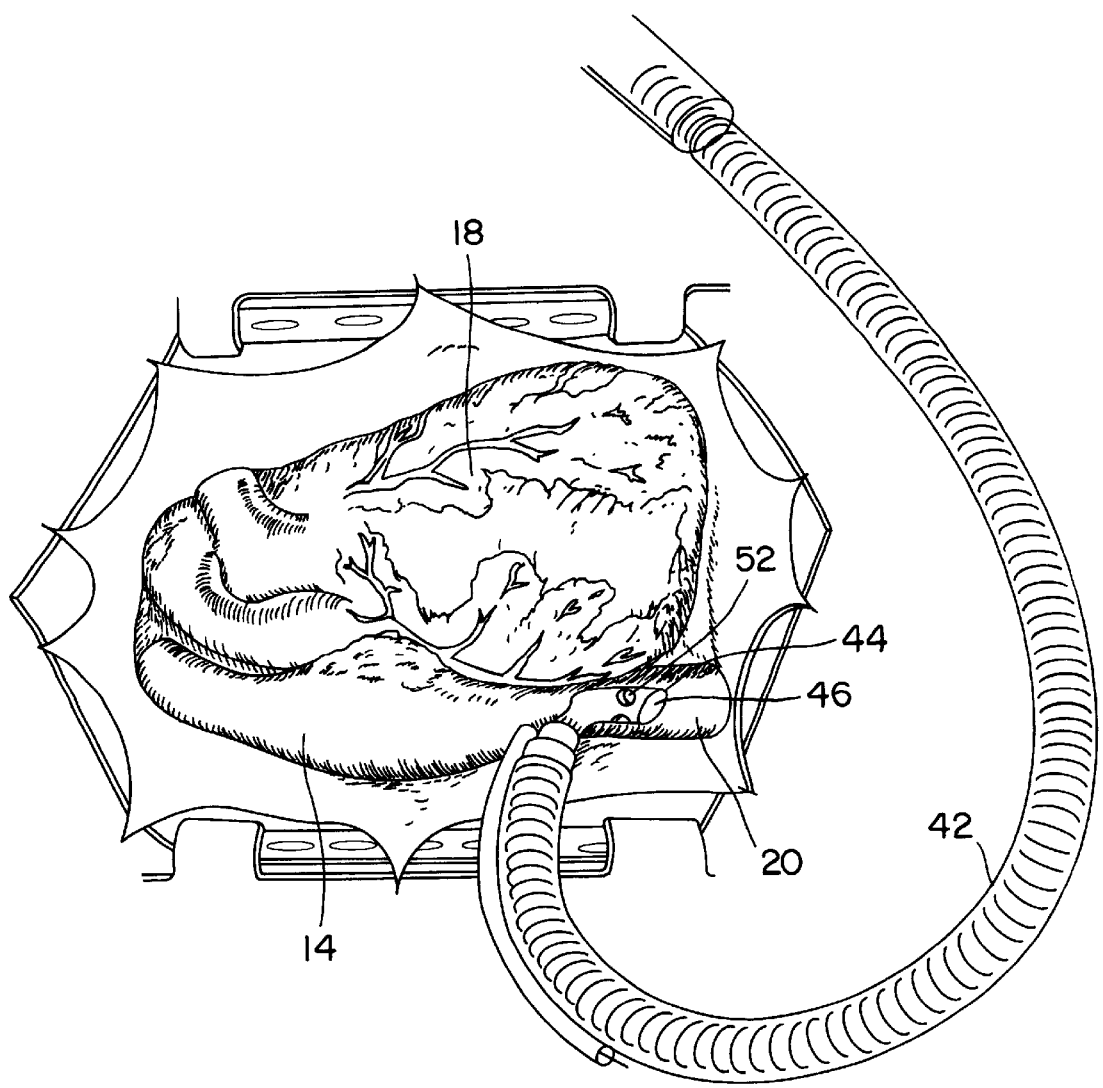
FIG. 7 is a perspective partial cut-away view of the cannula of FIG. 3 in use in a heart.

Distal end 36 is made of a relatively rigid material and is bent at an angle at apex 48. In one embodiment, shown in FIGS. 3 and 4, distal end 36 is bent at an angle of approximately 90° at apex 48. In other embodiments, distal end 36 may be bent at either an acute (FIG. 5) or obtuse angle (FIG. 6) depending of the physiology of the patient and the desired procedure to be performed.

As stated, distal end 36 is made of a relatively rigid material. Examples of the rigid material of distal end 36 include, but are not limited to, thin walled steel, thin walled rigid plastic and thin walled semi-rigid plastic. Semi-rigid means that the plastic may be soft or flexible but in an unstressed state, maintains its angled shape. Thin walled material is preferably used to minimize the outer diameter of distal end 36. This allows a smaller hole to be made through the right atrium 32 to place and maintain the cannula 34. It is preferable that a distance of about 3 to 5 cm. should extend distally beyond apex 48 to the ultimate distal end 44 of cannula 34.

Regardless of the angle of bending of the distal end 36 of cannula 34, at least one hole 50 is formed at the "heel" of apex 48. Hole 50 extends from the outside of cannula 34 at apex 48 to the interior lumen 40.

In one embodiment, the ultimate distal end 44 of cannula 34 is open so that interior lumen 40 is open at ultimate distal end 44. In another embodiment, ultimate distal end 44 is closed. In either embodiment, ultimate distal end 44 may be relatively abruptly terminated or may be "bullet" shaped or rounded to facilitate placement.

In addition to opening 46 at distal end 36, at least one, but preferably several, holes 52 are formed near the ultimate distal end 44 of cannula 34. Holes 52 extend from the outside of the distal end 36 to the lumen 40 of cannula 34. In use, when distal end 36 is placed through the heart 18 into the inferior vena cava 20 as described hereafter, holes 52 provide openings to allow blood to pass from the inferior vena cava 20 to the lumen 40. The blood in lumen 40 then flows through cannula 34 to exit cannula 34 through proximal end 38 to ultimately enter an extra-corporeal cardiac bypass system.

In the preferred embodiment, holes 52 are round but may also be elongated. Where the holes 52 are elongated, the axis of elongation of holes 52 is preferably aligned with lines that are parallel to the elongated axis of cannula 34. In addition, holes 52 are preferable equally spaced around the outer surface of cannula 34 near the ultimate distal end 44. Holes 52 may also be placed in several rows, each row spaced a different distance from the ultimate distal end 44 of distal end 36.

Where multiple holes 52 are provided, it may be preferable to alternate holes 52 in spacing around the outer surface of distal end 36 so that holes 52 in one row are offset from the holes 52 in another row.

As described above, in one embodiment, the ultimate distal end 44 of distal end 36 is closed so that opening 46 does not exist. In this embodiment, holes 52 still exist and are the only openings from outside the cannula 34 to the interior lumen 40 near the ultimate distal end 44.

The proximal end 54 of the rigid distal end 36 is attached to the distal end 56 of tubular body 40 through means well understood in the art including, but not limited to adhesives, friction fit, solvent bonding or ultrasonic welding. In addition, an adapter 58 (FIG. 6) may be placed between the tubular body 40 and distal end 36 to facilitate assembly. Although FIG. 6 only shows adapter 58, adapter 58 may be used in the other embodiments as well. In this way, a cannula 34 is formed having a flexible proximal end 38 made up primarily of tubular body 40 and a rigid distal end 36 having a right-angle configuration around apex 48.

In the preferred embodiment, the outer diameter of the distal end 36 of cannula 34 is about 0.450 inches. In addition, the entire length of the distal end 36, including the length of distal end 36 distal to apex 48, should be such that when the apex 48 is in the center of the right atrium as will be described hereafter, opening 46 will be in the inferior vena cava 20 slightly above the hepatic vein. Also in the preferred embodiment, the outer diameter of the tubular portion 40 of cannula 34 is equal to about 0.600 inches.

Hole 46, 50 and 52 may be formed at the time the distal end 36 is molded or formed or may be punched, drilled or otherwise cut through distal end 36 after distal end 36 has been formed. Distal end 36 is preferably made of stainless steel but may also be made of materials including, but not limited to, metals such as aluminum and titanium or glasses or fiberglasses or plastics.

Tubular body 42 is preferably made of a flexible material such as is common for cannulae used for medical uses. Examples of such material includes, but is not limited to, silicone, polyvinylchloride (PVC), polyurethane, polyether urethane, polyether urethane urea, polyamide, polyacetal, polyester, poly ethylene-chlorotrifluoroethylene, poly tetrafluoroethylene (PTFE or "Teflon®"), styrene butadiene rubber, polyethylene, polypropylene, polyphenylene oxide-polystyrene, poly-a-chloro-p-xylene, polymethylpentene, polysulfone and other related biostable polymers.

In use of cannula 34, a small opening 54 is cut into the right atrium 32. The distal end 36 of cannula 34 is inserted through opening 54 and is advanced through the right atrium 32 into the inferior vena cava 20. The ultimate distal end 44 of distal end 36 is positioned just above the hepatic vein (not shown). In this position, holes 50 are positioned near the junction of the inferior vena cava 20 and the right atrium 32 and holes 52 and opening 46 are in the inferior vena cava 20. In this position, the cannula 34 is kept away from the aorta and allows the cannula 34 to exit the right atrium 32 at opening 16 at an angle more perpendicular to the axis of the superior and inferior vena cavae 14, 20 than was previously possible.

Blood entering the right atrium 32 from the superior vena cava 14 is removed through holes 50. Blood entering the heart 1 8 through the inferior vena cava is removed through opening 46 or holes 52. Any blood passing opening 46 or holes 52 that enters the right atrium is removed through hole 50.

The invention has been shown and described in connection with a specific embodiment. It is to be realized, however, that the description given herein is for the purpose of illustrating the invention and is not intended to be limiting. It is further understood that improvements and modifications to the disclosure made herein will occur to those skilled in the art and that such improvements and modifications will still fall within the scope of the invention.

What is claimed is:

1. A two-staged venous cannula comprising:

an elongated tubular body having a distal end and a proximal end and an interior lumen extending from the distal end to the proximal end of the body, the interior lumen being open at the proximal end of the body, the tubular body having a flexible tubular proximal member and a rigid distal member, the rigid distal member formed in right angle around an apex, the flexible tubular proximal member and the rigid distal member joined together along a common axis so that the interior lumen passes through both the proximal member and the distal member, the distal member having an apex opening at the apex to allow fluid communication through the apex opening from outside the cannula into the interior lumen, the ultimate distal end of the distal member having at least one opening to allow fluid communication with the interior lumen.

2. The cannula of claim 1 wherein the interior lumen is open at the ultimate distal end of the distal member along an axis of elongation of the distal member.

3. The cannula of claim 1 wherein side openings extend through the distal member near the ultimate distal end, the side openings in fluid communication with the interior lumen.

* * * * *